US012766082B2

(12) United States Patent
Cotrell

(10) Patent No.: US 12,766,082 B2
(45) Date of Patent: Oct. 20, 2026

(54) PEARLIZING CONCENTRATE COMPOSITIONS AND METHODS OF PREPARATION THEREOF

(71) Applicant: Innospec Active Chemicals LLC, High Point, NC (US)

(72) Inventor: Phillip Loraine Cotrell, Salisbury, NC (US)

(73) Assignee: Innospec Active Chemicals LLC, High Point, NC (US)

( * ) Notice: Subject to any disclaimer, the term of this patent is extended or adjusted under 35 U.S.C. 154(b) by 0 days.

(21) Appl. No.: 17/961,008

(22) Filed: Oct. 6, 2022

(65) Prior Publication Data

US 2023/0108747 A1 Apr. 6, 2023

Related U.S. Application Data

(60) Provisional application No. 63/259,897, filed on Oct. 6, 2021.

(30) Foreign Application Priority Data

Oct. 28, 2021 (GB) ...................................... 2115485

(51) Int. Cl.

| | |
|---|---|
| ***A61K 8/46*** | (2006.01) |
| ***A61K 8/37*** | (2006.01) |
| ***A61K 8/44*** | (2006.01) |
| ***A61Q 5/02*** | (2006.01) |
| ***A61Q 19/00*** | (2006.01) |

(52) U.S. Cl.

CPC .............. *A61K 8/466* (2013.01); *A61K 8/375* (2013.01); *A61K 8/442* (2013.01); *A61K 8/447* (2013.01); *A61Q 5/02* (2013.01); *A61Q 19/00* (2013.01); *A61K 2800/436* (2013.01); *A61K 2800/596* (2013.01)

(58) Field of Classification Search

None

See application file for complete search history.

(56) References Cited

U.S. PATENT DOCUMENTS

| | | | | |
|---|---|---|---|---|
| 4,275,055 | A | 6/1981 | Nachtigal et al. | |
| 5,478,490 | A | 12/1995 | Russo et al. | |
| 6,165,955 | A | 12/2000 | Chen et al. | |
| 6,727,217 | B1 | 4/2004 | Nieendick et al. | |
| 2012/0149629 | A1 | 6/2012 | Dahms et al. | |
| 2019/0365619 | A1 | 12/2019 | Ceballos et al. | |
| 2020/0170894 | A1 * | 6/2020 | Park ....................... | A61K 8/466 |

FOREIGN PATENT DOCUMENTS

| | | | | |
|---|---|---|---|---|
| CA | 2129031 | A1 | 8/1993 | |
| EP | 3324927 | B1 | 7/2019 | |
| WO | WO1993/015171 | A1 | 8/1993 | |
| WO | WO 94/09763 | A1 | 5/1994 | |
| WO | WO-9621424 | A2 * | 7/1996 | ............. A61K 8/466 |
| WO | WO1997/013498 | A1 | 4/1997 | |
| WO | WO1998036048 | A1 | 8/1998 | |
| WO | WO 01/25378 | A2 | 4/2001 | |
| WO | WO 03/066796 | A1 | 8/2003 | |
| WO | WO 2004/028676 | A1 | 4/2004 | |
| WO | WO-2005075623 | A1 * | 8/2005 | ............... C11D 1/28 |
| WO | WO 2015/059711 | A1 | 4/2015 | |
| WO | WO 2015/090744 | A1 | 6/2015 | |

* cited by examiner

*Primary Examiner* — Bethany P Barham
*Assistant Examiner* — Judith Marie Kamm
(74) *Attorney, Agent, or Firm* — Jason A. Smith; Shumaker, Loop & Kendrick, LLP

(57) ABSTRACT

A concentrate composition useful as a pearlising agent for adding directly at ambient temperature to liquid chemical formulations such as personal cleaning formulations, laundry detergents, dishwashing detergents and hard surface cleaning compositions and comprising (a) at least 10 wt % of a glycol ester of a fatty acid; (b) at least one acyl alkyl isethionate surfactant of formula (I), having the chemical structure:

(I)

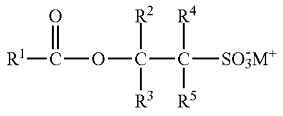

wherein $R^1$ represents an optionally substituted $C_4$-$C_{36}$ hydrocarbyl group, each of $R^2$, $R^3$, $R^4$ and $R^5$ independently represents hydrogen or a $C_1$-$C_4$ alkyl group, and wherein at least one of $R^2$, $R^3$, $R^4$ and $R^5$ is not hydrogen and $M^+$ represents a cation; and (c) at least one zwitterionic or amphoteric surfactant.

16 Claims, No Drawings

PEARLIZING CONCENTRATE COMPOSITIONS AND METHODS OF PREPARATION THEREOF

CROSS-REFERENCE TO RELATED APPLICATIONS

This application is a non-provisional application claiming priority to provisional application Ser. No. 63/259,897, filed Oct. 6, 2021 and to UK patent application Serial No. GB 2115485.1, filed Oct. 28, 2022. Each of these patent applications is hereby incorporated herein by reference in its entirety.

FIELD OF THE INVENTION

The present invention relates to concentrate compositions useful in the preparation of formulated products. In particular the invention relates to concentrate compositions for the preparation of pearlescent formulated products.

BRIEF DESCRIPTION OF THE INVENTION

Liquid compositions used in personal care and cleaning applications often desirably have an opaque iridescent appearance and may be referred to as "pearlised" or having a pearlescent finish. These formulations have high consumer appeal, and it is therefore common to add pearlising agents to a wide variety of different liquid chemical formulations. Pearlising agents are often added to personal cleansing formulations such as shampoos, body washes and liquid hand soaps; laundry detergents, dishwashing detergent compositions and other hard surface cleaning compositions.

Common pearlising agents include ethylene glycol monostearate (EGMS) and ethylene glycol distearate (EGDS). To achieve optimum pearl quality using these agents a formulated product must typically be heated to a temperature in excess of 70° C. in order to melt the ethylene glycol monostearate or distearate esters within the formulation. As the formulations cool the pearlising agents slowly crystallise to form insoluble particles that provide the pearl/opaque appearance. The rate of cooling and the rate of shear mixing as well as the size and shape of the mixing blade affect the crystal structure of the ester particles. Thus these factors have a significant impact on the quality and consistency of the pearl effect achieved. It is therefore essential to follow heating, cooling and shearing instructions strictly in order to achieve a uniform pearl effect for each batch of formulated product prepared. The often slow rates of cooling used means that pearlising is a very time consuming step. The process is also very energy intensive and costly due to the high temperature at which the formulation must be heated in order to melt the esters; the energy needed to obtain the desired cooling rate; and the energy needed for mixing and/or shearing.

Additionally the variability between batches of starting materials means that it can be difficult to obtain a consistently formulated product.

The present inventors have advantageously developed a concentrate pearlising composition which can be directly added to formulated compositions in order to provide a high quality pearl.

The concentrate composition of the invention can be mixed with the formulated composition at ambient temperature, avoiding the need to heat to 70° C. This advantageously saves formulators time and energy and provides improved product consistency.

DETAILED DESCRIPTION OF THE INVENTION

According to a first aspect of the present invention there is provided a concentrate composition comprising:

(a) at least 10 wt % of a glycol ester of a fatty acid;

(b) at least one acyl alkyl isethionate surfactant of formula (I):

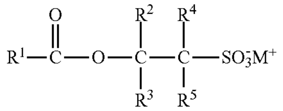

(I)

wherein $R^1$ represents an optionally substituted $C_4$-$C_{36}$ hydrocarbyl group;

each of $R^2$, $R^3$, $R^4$ and $R^5$ independently represents hydrogen or a $C_1$-$C_4$ alkyl group and wherein at least one of $R^2$, $R^3$, $R^4$ and $R^5$ is not hydrogen; and $M^+$ represents a cation; and (c) at least one zwitterionic or amphoteric surfactant.

Component (a) comprises a glycol ester of a fatty acid i.e. an ester of a fatty acid and a compound including at least two alcohol functional groups. Preferably component (a) comprises an ester of one or more glycols selected from ethylene glycol, propylene glycol and butylene glycol. Most preferably component (a) comprises ethylene glycol. The ester may be a monoester, a diester or a mixture thereof.

The fatty acid may be a saturated fatty acid, an unsaturated fatty acid or a mixture thereof. Preferably the fatty acid is a saturated fatty acid including a single carboxylic acid group. Preferably the fatty acid is a saturated monocarboxylic acid having 10 to 24 carbon atoms, preferably 12 to 20 carbon atoms, more preferably 16 to 18 carbon atoms.

Most preferably component (a) comprises a glycol ester of stearic acid (octadecanoic acid). Component (a) may comprise a monoester of stearic acid and/or a diester of stearic acid. Preferably component (a) comprises ethylene glycol monostearate (EGMS) and/or ethylene glycol distearate (EGDS).

The skilled person will appreciate that commercially available sources of stearic acid often comprise a mixture of stearic acid and one or more other acids, for example C16 acids. In one embodiment component (a) comprises a glycol ester, preferably an ethylene glycol ester of a mixture of fatty acids comprising from 50 to 60 wt % C16 fatty acids, from 40 to 50 wt % C18 fatty acids and 0 to 5 wt % C14 fatty acids.

This type of product is known to the person skilled in the art as a triple pressed stearic acid.

Component (a) is present in the concentrate composition of the present invention in an amount of at least 10 wt %. Preferably component (a) is present in an amount of at least 12 wt %, for example for at least 15 wt %. Component (a) may be present in the concentrate composition of the present invention in an amount of up to 50 wt %, preferably up to 40 wt %, for example up to 35 wt %.

Preferably component (a) is present in the concentrate composition of the present invention in an amount of from 10 to 35 wt %, preferably from 15 to 30 wt %, more preferably from 20 to 30 wt %.

When component (a) comprises a mixture of glycol esters, the above amounts refer to the total amount of all such compounds present in the composition.

In this specification, unless otherwise indicated any amounts referred to relate to the amount of active component present in the composition. The skilled person will appreciate that commercial sources of some of the components referred to herein may include impurities, side-products and/or residual starting material, as well as solvents or diluents. However, the amounts specified refer only to the active material and do not include any impurity, side-product, starting material, solvent or diluent that may be present.

Component (b) of the concentrate composition of the present invention comprises at least one acyl alkyl isethionate of formula (I).

Component (b) is present in the concentrate composition of the present invention in an amount of at least 0.01 wt %. Preferably component (b) is present in an amount of at least 0.1 wt %, for example for at least 0.5 wt %. Component (b) may be present in the concentrate composition of the present invention in an amount of up to 40 wt %, preferably up to 30 wt %, for example up to 20 wt %.

Preferably component (b) is present in the composition in an amount of from 0.1 to 18 wt %, preferably 0.5 to 15 wt %, more preferably from 1 to 12 wt %, for example about 1 to 10 wt %.

When component (a) comprises a mixture of compounds of formula (I), the above amounts refer to the total amount of all such compounds present in the composition.

In the formula (I), $R^1$ represents an optionally substituted $C_4$-$C_{36}$ hydrocarbyl group, $R^2$, $R^3$, $R^4$ and $R^5$ each independently represents hydrogen or a substituted or unsubstituted $C_1$-$C_4$ alkyl group, provided that at least one of $R^2$, $R^3$, $R^4$ and $R^5$ is not hydrogen, and $M^+$ represents a cation.

Suitably, $R^1$ represents an optionally substituted $C_4$-$C_{36}$ alkyl, $C_4$-$C_{36}$ alkenyl, $C_6$-$C_{12}$ aryl or $C_8$-$C_{22}$alkyl-$C_6$-$C_{12}$ aryl group. More suitably, $R^1$ represents an optionally substituted $C_4$-$C_{36}$ alkyl or $C_4$-$C_{36}$ alkenyl group, especially an optionally substituted $C_4$-$C_{36}$ alkyl group. Most suitably, $R^1$ represents a $C_4$-$C_{36}$ alkyl or $C_4$-$C_{36}$ alkenyl group, especially a $C_4$-$C_{36}$ alkyl group.

Suitably, $R^1$ represents an optionally substituted $C_4$-$C_{36}$ alkyl or $C_4$-$C_{36}$ alkenyl group, such as an optionally substituted $C_8$-$C_{18}$ alkyl or $C_8$-$C_{18}$ alkenyl group.

Suitably, $R^1$ represents a $C_4$-$C_{36}$ alkyl or $C_4$-$C_{36}$ alkenyl group, such as a $C_8$-$C_{18}$ alkyl or $C_8$-$C_{18}$ alkenyl group.

Suitably, $R^1$ represents an optionally substituted $C_5$-$C_{30}$ alkyl group, such as an optionally substituted $C_7$-$C_{24}$ alkyl group, for example an optionally substituted $C_7$-$C_{21}$ alkyl group, preferably an optionally substituted $C_7$-$C_{17}$-alkyl group.

Suitably, $R^1$ represents a $C_5$-$C_{30}$ alkyl group, such as a $C_7$-$C_{24}$ alkyl group, for example a $C_7$-$C_{21}$ alkyl group, preferably a $C_7$-$C_{17}$ alkyl group.

$R^1$ is suitably the residue of a fatty acid. Fatty acids obtained from natural oils often include mixtures of fatty acids. For example, the fatty acid obtained from coconut oil contains a mixture of fatty acids including $C_{12}$ lauric acid, $C_{14}$ myristic acid, $C_1$ palmitic acid, $C_8$ caprylic acid, $C_{10}$ capric acid and $C_{18}$ stearic and oleic acid.

$R^1$ may include the residue of one or more naturally occurring fatty acids and/or of one or more synthetic fatty acids. For example, $R^1$ may consist essentially of the residue of a single fatty acid.

Examples of carboxylic acids from which $R^1$ may be derived include coco acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Suitably $R^1$ comprises the residue of coco acid, the residue of mixed fatty acids derived from coconut oil or the residue of mixed fatty acids derived from palm kernel oil. More suitably, $R^1$ predominantly comprises the residue of a saturated fatty acid having 12 carbon atoms.

The acyl alkyl isethionate surfactant of the formula (I) may be prepared by any of the methods disclosed in the prior art, for example see the methods described in WO94/09763 and WO2005/075623.

In some embodiments only a single acyl alkyl isethionate surfactant of the formula (I) may be present in the concentrate composition of the first aspect. In some embodiments a mixture of two or more acyl alkyl isethionate surfactants of the formula (I) may be present. In such embodiments the above amounts refer to the total amounts of all acyl alkyl isethionate surfactants of the formula (I) present in the composition.

When any of $R^2$, $R^3$, $R^4$ and $R^5$ represents an optionally substituted $C_1$-$C_4$ alkyl group, the alkyl group is suitably n-propyl, ethyl or methyl, such as ethyl or methyl, most preferably methyl.

Preferably one of the groups $R^2$, $R^3$, $R^4$ and $R^5$ represents an optionally substituted $C_1$-$C_4$ alkyl group and the remaining groups represent hydrogen. For example, $R^2$ may represent an optionally substituted $C_1$-$C_4$ alkyl group and $R^3$, $R^4$ and $R^5$ may all represent hydrogen. For example, $R^4$ may represent an optionally substituted $C_1$-$C_4$ alkyl group and $R^2$, $R^3$ and $R^5$ may all represent hydrogen.

Preferably, $R^2$ represents a $C_1$-$C_4$ alkyl group and $R^3$, $R^4$ and $R^5$ all represent hydrogen. Preferably, $R^4$ represents a $C_1$-$C_4$ alkyl group and $R^2$, $R^3$ and $R^5$ all represent hydrogen.

Most preferably, $R^2$ represents a methyl group and $R^3$, $R^4$ and $R^5$ all represent hydrogen. Most preferably, $R^4$ represents a methyl group and $R^2$, $R^3$ and $R^5$ all represent hydrogen.

Preferably component (b) comprises an acyl alkyl isethionate surfactant of formula (I) selected from one or more of sodium lauroyl methyl isethionate, sodium cocoyl methyl isethionate and sodium oleoyl methyl isethionate. Sodium lauroyl methyl isethionate (SLMI) is especially preferred.

Suitably, $M^+$ represents a metal cation or an optionally substituted ammonium cation, preferably a metal cation. By "optionally substituted ammonium cation", we mean to refer to an ammonium cation wherein the nitrogen atom may be substituted with from 1 to 4 optionally substituted hydrocarbyl groups. Suitable ammonium cations include those derived from alkyl amines and alkanolamines. Preferred ammonium cations include isopropanolamine, isopropylamine, ethanolamine, diethanolamine, triethanolamine and 2-amino-2-methyl-1,3-propanediol (AMPD). Preferred ammonium cations include $NH_4^+$ and the ammonium cation of triethanolamine.

Suitable metal cations include alkali metal cations, for example sodium, lithium and potassium cations, and alkaline earth metal cations, for example calcium and magnesium cations. Suitably, $M^+$ represents an alkali metal cation or an optionally substituted ammonium cation. Preferably, $M^+$ represents a zinc, potassium or sodium cation. Most preferably, $M^+$ represents a sodium cation.

The skilled person will appreciate that when $M^+$ is a divalent metal cation two moles of anion will be present for each mole of cation.

The acyl alkyl isethionate surfactant of formula (I) may comprise the reaction product of sodium methyl isethionate and a fatty acid, that is a compound of formula $R^1COOCHR^2CHR^4SO_3^-M^+$ in which one of $R^2$ and $R^4$ is methyl and the other is hydrogen. Mixtures of these isomers may be present.

The solid cleansing composition of the present invention may include a mixture of more than one acyl alkyl isethionate surfactant of formula (I). For example, an isomeric mixture of acyl alkyl isethionate surfactants of formula (I) may be present. Such a mixture may include, for example an acyl alkyl isethionate surfactant in which $R^2$ represents a $C_1$-$C_4$ alkyl group (suitably methyl) and $R^3$, $R^4$ and $R^5$ are all hydrogen and an acyl alkyl isethionate surfactant in which $R^4$ represents a $C_1$-$C_4$ alkyl group (suitably methyl) and $R^2$, $R^3$ and $R^5$ are all hydrogen.

In particular, the concentrate composition of the present invention may comprise a mixture of isomers, that is a compound of formula $R^1COOCH_2CHR^4SO_3^-M^+$ in which $R^4$ represents a $C_1$-$C_4$ alkyl group (preferably methyl) and a compound of formula $R^1COOCHR^2CH_2SO_3^-M^+$ in which $R^2$ represents a $C_1$-$C_4$ alkyl group (preferably methyl).

Suitably such mixtures comprise approximately 90% of compounds in which $R^2$ is methyl and $R^4$ is hydrogen and approximately 10% of compounds in which $R^2$ is hydrogen and $R^4$ is methyl.

Component (c) comprises an amphoteric or zwitterionic surfactant.

Component (c) is present in the concentrate composition of the present invention in an amount of at least 0.01 wt %. Preferably component (c) is present in an amount of at least 0.1 wt %, for example for at least 0.5 wt %. Component (c) may be present in the concentrate composition of the present invention in an amount of up to 40 wt %, preferably up to 30 wt %, for example up to 20 wt %.

Component (c) is preferably present in the composition of the present invention in an amount of from 0.1 to 30 wt %, preferably from 0.5 to 25 wt %, more preferably from 1 to 20 wt %, more preferably from 3 to 18 wt %, for example 5 to 15 wt %.

In some embodiments component (c) comprises a mixture two or more amphoteric and/or zwitterionic surfactants. In such embodiments, the above amounts refer to the total amount of all zwitterionic and/or amphoteric surfactants present in the composition.

Suitable amphoteric surfactants for use in compositions of the first aspect of the invention include those based on fatty nitrogen derivates and those based on betaines.

Suitable amphoteric or zwitterionic surfactants may be selected from betaines, for example alkyl betaines, alkylamidopropyl betaines, for example cocamidopropyl betaine, alkylamidopropyl hydroxy sultaines, alkylamphoacetates, alkylamphodiacetates, alkyl propionates, alkylamphodipropionates, alkylamphopropionates, alkyliminodipropionates and alkyliminodiacetate.

Amphoteric or zwitterionic surfactants for use in compositions of the first aspect may include those which have an alkyl or alkenyl group of 7 to 22 carbon atoms and comply with an overall structural formula:

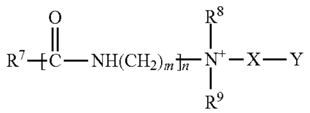

where $R^7$ is alkyl or alkenyl of 7 to 22 carbon atoms; $R^8$ and $R^9$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Amphoteric or zwitterionic surfactants may include simple betaines of formula:

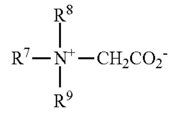

and amido betaines of formula:

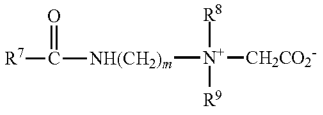

where m is 2 or 3.

In both formulae $R^7$, $R^8$ and $R^9$ are as defined previously. $R^7$ may, in particular, be a mixture of $C_{12}$ and $C_{14}$ alkyl groups derived from coconut so that at least half, preferably at least three quarters, of the groups $R^7$ has 10 to 14 carbon atoms. $R^8$ and $R^9$ are preferably methyl.

Amphoteric or zwitterionic surfactants may include sulfobetaines of formula:

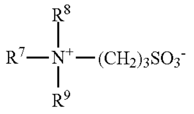

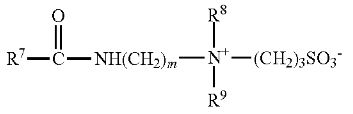

where m is 2 or 3, or variants of these in which $-(CH_2)_3SO_3$ is replaced by

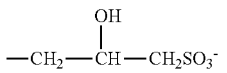

where $R^7$, $R^8$ and $R^9$ in these formulae are as defined previously.

Amphoteric or zwitterionic surfactants may include amphoacetates and diamphoacetates.

Amphoacetates generally conform to the following formula:

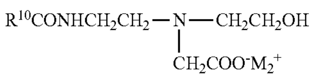

Diamphoacetates generally conform to the following formula:

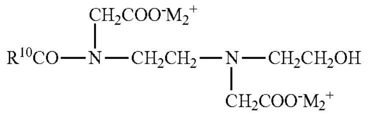

where $R^{10}$ is an aliphatic group of 8 to 22 carbon atoms and $M_2^+$ is a cation such as sodium, potassium, ammonium, or substituted ammonium.

Suitable acetate-based surfactants include lauroamphoacetate; alkyl amphoacetate; sodium alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N, N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; alkamidopropyl hydroxyl sultaine; cocamidopropyl hydroxyl sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate surfactants include acyl glycinates such as cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N—$C_{10/12}$ fatty acid amidoethyl-N-(2-hydroxyethyl)-glycinate; N—$C_{12/18}$-fatty acid amidoethyl-N-(2-hydroxyethyl)-glycinate; dihydroxyethyl tallow gycinate.

Preferred acetate-based amphoteric surfactants for use as component (c) include sodium lauroamphoacetate, disodium lauroamphoacetate and mixtures thereof.

Preferred betaine surfactants for use as component (c) include cocoamidopropyl betaine.

Preferred sultaine surfactants for use as component (c) include cocoamidopropylhydroxy sultaine.

Preferably component (c) comprises cocoamidopropyl betaine and/or cocoamidopropylhydroxy sultaine.

In preferred embodiments the weight ratio of component (a) to component (b) present in the composition of the present invention is from 50:1 to 1:2, preferably from 40:1 to 1:1.5, more preferably from 30:1 to 1:1.

Preferably the weight ratio of component (a) to component (c) present in the composition of the present invention is from 20:1 to 1:5, preferably from 10:1 to 1:2, more preferably from 6:1 to 1:1.

Preferably the weight ratio of component (b) to component (c) present in the composition of the present invention is from 10:1 to 1:10, more preferably from 4:1 to 1:4.

The concentrate composition of the first aspect may comprise one or more further components. Preferably the one or more further components are selected from chelating agents, preservatives, pH modifiers, hydrotropes and further surfactants.

The concentrate composition of the first aspect may comprise a chelating agent. Suitable chelating agents include ethylenediamine-N,N'-disuccinic acid, methylglycinediacetic acid, glutamic acid N,N-diacetic acid, imino disuccinic acid, diethylene triamine pentaacetic acid, ethylenediamine tetraacetic acid, diethylenetriamine penta methylene phosphonic acid, etidronic acid and anions, salts and mixtures thereof.

Preferred chelating agents are biodegradable chelating agents for example ethylenediamine-N,N'-disuccinic acid, methylglycinediacetic acid, glutamic acid N,N-diacetic acid, imino disuccinic acid and anions and mixtures thereof. Ethylenediamine-N,N'-disuccinic acid (EDDS) is especially preferred. The skilled person will appreciate that polycarboxylic acid chelating agents may be present as the free acid or a salt thereof.

The concentrate composition of the invention may comprise a preservative. Suitable preservatives will be known to the person skilled in the art and include sodium benzoate, potassium sorbate, sorbic acid, phenoxyethanol, benzyl alcohol, DMDM hydantoin, imidazolidinyl urea, methylchloroisothiazolinone, methylisothiazolinone, salicylic acid, benzyl salicylate, methylparaben, propylparaben and caprylyl glycol. A preferred preservative for use herein is sodium benzoate.

The concentrate composition of the invention may comprise a hydrotrope. Suitable hydrotropes will be known to the person skilled in the art and include propylene glycol, hexylene glycol, glycerine, sorbitol, xylene sulfonates, cumene sulfonates, ethanol, urea, dipropylene glycol. A preferred hydrotrope for use herein is sorbitol.

The concentrate composition of the invention may comprise a pH modifier. Suitable pH modifiers will be known to the person skilled in the art and include lactic acid, potassium hydroxide sodium hydroxide, sodium carbonate, triethanolamine and sodium gluconate. A preferred pH modifier is citric acid.

Preferably the composition of the present invention has a pH of from 3 to 9, preferably 4 to 8, for example 4.5 to 7.5.

In some embodiments the composition has a pH of 4.5 to 5.5.

In some embodiments the composition has a pH of 6.5 to 7.5.

The concentrate composition of the invention may comprise one or more further surfactants.

Such surfactants may be selected from anionic surfactants, cationic surfactants, non-ionic surfactants and mixtures thereof. The selection of suitable further surfactants for use in the composition of the present invention is within the competence of the person skilled in the art.

Suitable anionic surfactants for use in compositions of the first aspect of the invention include salts of $C_{12}$-$C_{18}$ carboxylic acids, ethoxylated carboxylic acids, ester carboxylates and ethoxylated ester carboxylates and sarcosinates. Other suitable anionic surfactants include sulfates and sulfonates, for example alkyl sulfates, alkyl ether sulfates, alcohol sulfates, alcohol ether sulfates, α-olefin sulfonates, linear alkyl sulfonates; and phosphate esters.

Suitable anionic surfactants may be selected from salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, acyl isethionates, non-acylated alkyl isethionates; fatty acid taurates; acyl taurates; amino acid surfactants such as glutamates and glycinates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids and salts of lipoamino acids. Particularly exemplary salts of the above, where applicable, are the sodium, potassium, ammonium, magnesium and triethanolamine salts. Suitable ammonium cations include those derived from alkyl amines and alkanolamines. Preferred ammonium cations include isopropanolamine, isopropylamine, ethanolamine, diethanolamine, triethanolamine and 2-amino-2-methyl-1,3-propanediol (AMPD). Preferred ammonium cations include $NH_4^+$ and the ammonium cation of triethanolamine.

Preferred anionic surfactants are selected from salts of fatty acids; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, acyl isethionates, non-acylated alkyl isethionates; fatty acid taurates; acyl taurates; amino acid surfactants such as glutamates and glycinates; products of condensation of fatty acids with oxy- and aminoalkanesulfonic acids; alkyl and acyl sarcosinates; sulfoacetates; alkyl phosphates; alkyl phosphate esters; acyl lactates; and salts of lipoamino acids. Particularly exemplary salts of the above, where applicable, are the sodium, potassium, ammonium, magnesium and triethanolamine salts. Suitable ammonium cations include those derived from alkyl amines and alkanolamines. Preferred ammonium cations include isopropanolamine, isopropylamine, ethanolamine, diethanolamine, triethanolamine and 2-amino-2-methyl-1,3-propanediol (AMPD). Preferred ammonium cations include $NH_4^+$ and the ammonium cation of triethanolamine.

Suitable sulfoacetates include acyl sulfoacetates, particularly sodium acyl sulfoacetates.

Suitable glutamate surfactants include acyl glutamates.

Acyl isethionates for use in compositions of the first aspect of the invention may be of the formula (II):

(II)

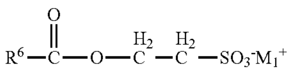

wherein $R^6$ represents an optionally substituted $C_4$-$C_{36}$ hydrocarbyl group; and $M_1^+$ represents a cation.

Suitably, $R^6$ represents an optionally substituted $C_4$-$C_{36}$ alkyl, $C_4$-$C_{36}$ alkenyl, $C_6$-$C_{12}$ aryl or $C_8$-$C_{22}$ alkyl-$C_6$-$C_{12}$ aryl group. More suitably, $R^6$ represents an optionally substituted $C_4$-$C_{36}$ alkyl or $C_4$-$C_{36}$ alkenyl group. Most suitably, $R^6$ represents a $C_4$-$C_{36}$ alkyl group or $C_4$-$C_{36}$ alkenyl group, especially a $C_4$-$C_{36}$ alkyl group.

Suitably, $R^6$ represents an optionally substituted $C_5$-$C_{30}$ alkyl group, such as an optionally substituted $C_7$-$C_{24}$ alkyl group, for example an optionally substituted $C_7$-$C_{21}$ alkyl group, preferably an optionally substituted $C_7$-$C_{17}$alkyl group.

Suitably, $R^6$ represents a $C_5$-$C_{30}$ alkyl group, such as a $C_7$-$C_{24}$ alkyl group, for example a $C_7$-$C_{21}$ alkyl group, preferably a $C_7$-$C_{17}$ alkyl group.

$R^6$ is suitably the residue of a fatty acid. Fatty acids obtained from natural oils often include mixtures of fatty acids. For example, the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic acid.

$R^6$ may include the residue of one or more naturally occurring fatty acids and/or of one or more synthetic fatty acids. For example, $R^6$ consists essentially of the residue of a single fatty acid.

Examples of carboxylic acids from which $R^6$ may be derived include coco acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Suitably $R^6$ comprises the residue of coco acid, the residue of mixed fatty acids derived from coconut oil or the residue of mixed fatty acids derived from palm kernel oil.

Suitably, $M_1^+$ represents a metal cation or an optionally substituted ammonium cation, preferably a metal cation. Suitable ammonium cations include $NH_4^+$ and the ammonium cation of triethanolamine. Suitable ammonium cations include those derived from alkyl amines and alkanolamines. Preferred ammonium cations include isopropanolamine, isopropylamine, ethanolamine, diethanolamine, triethanolamine and 2-amino-2-methyl-1,3-propanediol (AMPD). Preferred ammonium cations include $NH_4^+$ and the ammonium cation of triethanolamine.

Suitable metal cations include alkali metal cations, for example sodium, lithium and potassium cations, and alkaline earth metal cations, for example calcium and magnesium cations.

Preferably $M_1^+$ represents a zinc, potassium or sodium cation. Most preferably $M_1^+$ represents a sodium cation.

The skilled person will appreciate that when $M_1^+$ is a divalent metal cation two moles of anion will be present for each mole of cation.

In some embodiments only a single acyl isethionate of the formula (II) may be present in the solid cleansing composition of the first aspect. In some embodiments a mixture of two or more acyl isethionates of the formula (II) may be present.

For example, the acyl isethionates of the formula (II) may be selected from one or more of sodium lauroyl isethionate, sodium cocoyl isethionate and sodium myristoyl isethionate. Sodium cocoyl isethionate is especially preferred.

Preferred additional anionic detersive surfactants for use in compositions of the first aspect of the invention include alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable non-ionic surfactants for use in compositions of the first aspect of the invention include alcohol alkoxylates such as alcohol ethoxylates, alcohol propoxylates, and ethylene oxide/propylene oxide copolymer derived surfactants, aliphatic esters, aromatic esters, sugar esters, especially sorbitan esters, alkyl polyglucosides, fatty acid alkoxylates such as fatty acid ethoxylates and fatty acid propoxylates or polyethylene glycol esters and partial esters, glycerol esters including glycerol partial esters and glycerol triesters, fatty alcohols (such as cetearyl alcohol, lauryl alcohol, stearyl alcohol, behenyl alcohol), alkanolamides and amineoxides.

Suitable non-ionic surfactants may be selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenol-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine); long chain tertiary amine oxides, long chain tertiary phosphine oxides and dialkyl sulfoxides; alkyl amine oxides, alkyl amido amine oxides; alkyl tertiary phosphine oxides; alkoxyl alkyl amines; sorbitan; sorbitan esters; sorbitan ester alkoxylates; glycerol ester alkoxylates; sucrose esters; sugar amides, such as a polysaccharide amide; lactobionamides; and alkyl polysaccharide nonionic surfactants, for example alkylpolyglycosides.

Suitable cationic surfactants for use in compositions of the first aspect of the invention are typically based on fatty amine derivates or phosphonium quaternary ions, and quaternary ammonium compounds. Polymeric cationic surfactants may also be used.

Suitable cationic surfactants for use in compositions of the first aspect of the invention include tertiary amine salts, mono alkyl trimethyl ammonium chloride, mono alkyl trimethyl ammonium methyl sulfate, dialkyl dimethyl ammonium chloride, dialkyl dimethyl ammonium methyl sulfate, trialkyl methyl ammonium chloride and trialkyl methyl ammonium methyl sulfate.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen (e.g. bromide), acetate, citrate, lactate, glycolate, phosphate nitrate, sulfate, or alkylsulfate.

Further suitable cationic surfactants include those materials having the CTFA designations Quaternium-5, Quaternium-31 and Quaternium-18. Mixtures of any of the foregoing materials may also be suitable. A particularly useful cationic surfactant for use as a hair conditioning agent is cetyltrimethylammonium chloride, available commercially, for example as GENAMIN CTAC, ex Hoechst Celanese.

Salts of primary, secondary, and tertiary fatty amines are also suitable cationic surfactants. The alkyl groups of such amines preferably have from 12 to 22 carbon atoms, and can be optionally substituted.

Useful cationic surfactants include amido substituted tertiary fatty amines, in particular tertiary amines having one $C_{12}$ to $C_{22}$ alkyl or alkenyl chain. Such amines include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachid amidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, Ntallowpropane diamine, ethoxylated (with 5 moles of ethylene oxide) stearylamine, dihydroxyethylstearylamine, and arachidyl behenylamine.

These amines are typically used in combination with an acid to provide the cationic species. Suitable acids include L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid.

Other useful cationic amine surfactants include those disclosed in U.S. Pat. No. 4,275,055.

Suitable polymeric cationic surfactancts include polyquaternium-7, polyquaternium-10, polyquaternium-11, guar hydroxypropyltrimonium chloride, and hydroxypropyl guar hydroxypropyltrimonium chloride.

In some preferred embodiments the concentrate composition of the first aspect comprises less than 2.5 wt % sulfate containing surfactants, preferably less than 2 wt %, more preferably less than 1.5 wt %, preferably less than 1 wt %, suitably less than 0.75 wt %, more preferably less than 0.5 wt %, preferably less than 0.25 wt %, preferably less than 0.1 wt %, suitably less than 0.05 wt %, for example less than 0.01 wt %, preferably less than 0.005 wt % and most preferably less than 0.001 wt %.

In some embodiments the concentrate composition of the first aspect of the present invention is preferably free of sulfate containing surfactants.

In some preferred embodiments components (b) and (c) together comprise at least 70 wt % of all surfactants present in the concentrate composition of the first aspect, preferably at least 75 wt %, more preferably at least 80 wt %, suitably at least 85 wt %, more preferably at least 90 wt %.

The concentrate composition of the present invention is preferably an aqueous composition.

In some embodiments the composition may comprise one or more further solvents in addition to water. Such suitable co-solvents will be known to the person skilled in the art.

However in preferred embodiments water is the major solvent present in the concentrate composition of the present invention and suitably comprises at least 80 wt % of all solvents present, preferably at least 90 wt %, more preferably at least 95 wt %.

In some preferred embodiments the concentrate composition of the first aspect of the present invention is an aqueous composition comprising:

from 10 to 40 wt % component (a);

from 0.1 to 20 wt % component (b);

from 1 to 25 wt % component (c); and optionally one or more further components are selected from chelating agents, preservatives, pH modifiers, hydrotropes and further surfactants.

In some preferred embodiments the concentrate composition of the first aspect of the present invention is an aqueous composition comprising:

from 15 to 30 wt % component (a);

from 1 to 12 wt % component (b);

from 5 to 15 wt % component (c); and optionally one or more further components are selected from chelating agents, preservatives, pH modifiers, hydrotropes and further surfactants.

The concentrate composition of the first aspect of the present invention may be an opaque composition.

The concentrate composition of the first aspect of the present invention is preferably a pearlescent composition.

The concentrate composition of the first aspect is preferably a liquid composition or semi-liquid composition. It may be a thick viscous liquid in the form of a thick paste or it may be a runny liquid. Preferably the concentrate composition is flowable and pumpable.

Preferably the concentrate composition of the first aspect has a Brookfield Viscosity at 25° C. measured using a No 5 spindle @ 2.5 RPM of from 1000 to 100000 cps, preferably from 1000 to 50000 cps.

The concentrate composition of the first aspect of the present invention is highly advantageous because it can be added to a composition which is almost fully formulated to provide a pearl effect without the need for complex heating, cooling or shearing steps.

The concentrate composition of the invention can be added in a small amount to a formulation with simple mixing under ambient conditions.

The concentrate composition of the present invention is suitably made by heating the components and slowing cooling with agitation. Heating a concentrated mixture is much more energy efficient than heating a final formulated product. Furthermore addition of a concentrate composition at ambient temperature means that a formulator does not need to use a long, complex heating and cooling process.

According to a second aspect of the present invention, there is provided a method of preparing a concentrate composition, the method comprising the steps of:

(i) admixing the following components:

(a) at least 10 wt % of a glycol ester of a fatty acid;

(b) at least one acyl alkyl isethionate surfactant of formula (I):

(I)

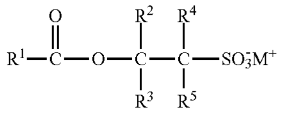

wherein $R^1$ represents an optionally substituted $C_4$-$C_{36}$ hydrocarbyl group; each of $R^2$, $R^3$, $R^4$ and $R^5$ independently represents hydrogen or a $C_1$-$C_4$ alkyl group and wherein at least one of $R^2$, $R^3$, $R^4$ and $R^5$ is not hydrogen; and $M^+$ represents a cation; and (c) at least one zwitterionic or amphoteric surfactant;

(ii) heating the mixture obtained in step (i) to a temperature of at least 60° C.; and (iii) slowly cooling the composition.

Step (i) may involve adding one or more further components. Preferably the one or more further components are selected from chelating agents, preservatives, pH modifiers, hydrotropes and further surfactants. These are suitably as defined in relation to the first aspect.

Preferably water is added in step (i) to provide an aqueous composition. Optionally one ore more further solvents may be added, for example one or more water miscible solvents. In preferred embodiments water is the only solvent used.

Preferred features of the second aspect are as defined in relation to the first aspect.

The mixture is heated in step (ii) to a temperature of at least 60° C. Preferably the mixture is heated to a temperature of at least 70° C., for example at least 75° C.

Preferably the composition is agitated as it is cooled during step (iii), preferably by the application of shear forces.

The selection of suitable shear rates and cooling profiles will be within the competence of the person skilled in the art. Guidance is provided for example in WO200125378, WO2003066796, WO2004028676A1 and WO2011023803.

For example the skilled person would understand that cooling and/or shearing rates help control crystallisation; preferably the ester crystallizes into platelet structures. Larger platelet structures are preferred for pearlescent formulations.

According to a third aspect of the present invention there is provided a method of providing a pearlescent finish to a formulation, the method comprising admixing into the formulation a pearlising composition comprising:

(a) at least 10 wt % of a glycol ester of a fatty acid;

(b) at least one acyl alkyl isethionate surfactant of formula (I):

(I)

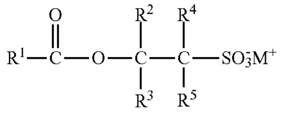

wherein $R^1$ represents an optionally substituted $C_4$-$C_{36}$ hydrocarbyl group; each of $R^2$, $R^3$, $R^4$ and $R^5$ independently represents hydrogen or a $C_1$-$C_4$ alkyl group and wherein at least one of $R^2$, $R^3$, $R^4$ and $R^5$ is not hydrogen; and $M^+$ represents a cation; and (c) at least one zwitterionic or amphoteric surfactant.

Preferred features of the third aspect are as defined in relation to the first and second aspects.

By "formulation" we mean to refer to a chemical composition which contains multiple components which have been mixed together. The formulation is suitably prepared to contain specific ingredients and has a particular purpose. For example the formulation may be a cleaning composition or a personal care composition. The types of components that are typically present in such compositions will be known to the person skilled in the art.

For example laundry and dishwashing compositions typically comprise ingredients such as surfactants, builders, bleaches, bleach activators, redeposition additives, dye transfer inhibitors, enzymes, colorants and fragrances.

Personal care compositions typically comprise ingredients such as surfactants (including anionic, amphoteric, nonionic and cationic surfactants); conditioning agents (including quaternary ammonium compounds, cationic polymers, cationic conditioning polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone etc).

The formulation is preferably a liquid composition or semi-liquid composition. It may be a thick viscous liquid in the form of a thick paste or it may be a runny liquid. Preferably the concentrate composition is flowable and pumpable.

Preferably the formulation provided by the method of the third aspect comprises 0.1 to 3 wt %, suitably 0.5 to 2 wt %, preferably 0.5 to 1.5 wt % of component (a).

Preferably the method of the third aspect is carried out at a temperature of less than 60° C., preferably less than 50° C., more preferably less than 40° C., preferably less than 30° C.

Preferably the formulation is not heated in the method of the third aspect of the present invention.

In some embodiments, preferably the formulation is not initially opaque or pearlescent.

The product obtained by the method of the third aspect is a pearlised/pearlescent formulated product.

The method of the third aspect preferably increased the opacity of the formulated product.

According to a fourth aspect of the present invention there is provided a method of preparing a pearlescent formulation, the method comprising:

(x) preparing a formulation which is not pearlescent; and (y) adding a concentrate composition of the first aspect to the formulation prepared in step (x).

Preferably the concentrate composition of the first aspect used in step (y) is prepared by the method of the second aspect.

According to a fifth aspect of the present invention there is provided the use of a composition comprising:

(a) at least 10 wt % of a glycol ester of a fatty acid;

(b) at least one acyl alkyl isethionate surfactant of formula (I):

(I)

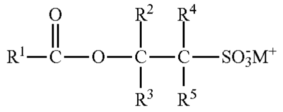

wherein $R^1$ represents an optionally substituted $C_4$-$C_{36}$ hydrocarbyl group; each of $R^2$, $R^3$, $R^4$ and $R^5$ independently represents hydrogen or a $C_1$-$C_4$ alkyl group and wherein at least one of $R^2$, $R^3$, $R^4$ and $R^5$ is not hydrogen; and $M^+$ represents a cation; and (c) at least one zwitterionic or amphoteric surfactant; as a pearlising agent.

Preferred features of the fourth and fifth aspects are as defined in relation to the first, second and third aspects.

The present invention relates to providing a composition with a pearlescent finish. Preferably the pearlescent effect provided by the invention is consistent and can be readily reproduced under the same conditions. Such a pearlescent effect can be assessed visually by the skilled person.

In some embodiments the present invention may be used to increase the pearlescence of a composition.

The invention will now be further defined with the reference to the following non-limiting examples.

EXAMPLES

The compositions of table 1 were prepared comprising the listed ingredients, according to the method below:

TABLE 1

| | | Composition | | | | | | | |
|---|---|---|---|---|---|---|---|---|---|
| | Component | 1 (wt % active) | 2 (wt % active) | 3 (wt % active) | 4 (wt % active) | 5 (wt % active) | 6 (wt % active) | 7 (wt % active) | 8 (wt % active) |
| A | Sodium Benzoate | 0.491 | 0.5 | 0.49 | 0.5 | 0.5 | 0.5 | 0.5 | 0.5 |
| A | EDDS | 0.207 | 0.209 | 0.205 | 0.205 | 0.198 | 0.19 | 0.19 | 0.19 |
| A | CAPB | | | | 7.5 | 7.2 | 7.2 | 7.05 | 7.2 |
| A | CAPHS | 11.64 | 10 | 9.8 | | | | | |
| A | Sorbitol | 3.15 | 3.5 | 3.43 | 3.5 | 3.36 | | | |
| B | Citric Acid | 0.25 | QS | QS | QS | 0.2 | 0.15 | 0.1 | 0.25 |
| C | SLMI | 6.188 | 5.95 | 5.831 | 5.95 | 5.695 | 5.695 | 5.61 | 5.525 |
| D | EGDS | 18.2 | 20 | 24.52 | 25 | 24 | 24 | 23.5 | 30 |
| E | Deionised water | To 100 | To 100 | To 100 | To 100 | To 100 | To 100 | To 100 | To 100 |

Sodium benzoate was provided as a 100% active ingredient.

EDDS was provided as a 38 wt % aqueous solution of the trisodium salt of ethylenediamine-N,N'-disuccinic acid.

CAPB was provided as a 30 wt % aqueous solution of cocamidopropyl betaine.

CAPHS was provided as a 30 wt % aqueous solution of cocamidopropyl hydroxysultaine.

Sorbitol was provided as a 70 wt % aqueous solution.

Citric Acid was provided as a 50 wt % aqueous solution.

SLMI was provided as a solid ingredient comprising 85 wt % active sodium lauroyl methyl isethionate.

EGDS was provided as a commercially available product comprising predominately ethylene glycol distearate and minor amounts of the monostearate product.

Method

1. Combine "A" ingredients. With smooth, mechanical agitation, mix until completely uniform. As detailed above several of the component A ingredients were provided in as aqueous solutions. The amounts of the component A ingredients referred to in table 1 are the amounts of active component present, ignoring any solvent or diluent present. However in step 1 such water is included and further water may also be added at this stage.
2. With smooth mechanical agitation adjust pH of system to 4.8-5.2 with 50% aqueous citric acid as needed. With smooth agitation warm system to 50° C.
3. With Smooth agitation slowly blend in flakes of sodium lauroyl methyl isethionate. Mix until completely clear and uniform. With smooth agitation, continue heating the system to 70-80° C.
4. With rapid but smooth agitation blend EGDS/EGMS flakes into the heated system. Continue heating to 80-85° C. Maintain 80-85° C. temperature with mixing for 20 minutes and then remove heat source. Continue cooling to 45-50° C. with rapid but smooth agitation.
5. With rapid but smooth agitation, slowly blend in 20-25° C. water. Further water is added at this stage to provide a 100% of the components listed in table 1 for each composition. However some water will have already been added as part of the component A ingredients and optionally additionally in step 1. Mix until completely uniform. Continue to cool system to 25-30° C. with rapid but smooth agitation. Package at 20-25° C.

Pearlising Effect

The pearlising effect of the compositions of examples 3 to 8 was assessing by adding 6 g of each concentrated composition to 194 g deionised water and 1 drop of food colouring.

The ingredients were combined at room temperature and with mechanical agitation mixed until the cold pearl concentrate is completely dispersed. The resulting system was visually observed and assessed for pearl quality. The following rating system was used:

Rating Scale

Poor=Opaque Liquid with no Pearl Appearance

Moderate=Opaque Liquid with slight pearl appearance

Good=Opaque liquid with moderate pearl appearance

Excellent=Opaque liquid with high sheen, pearl appearance

The results are shown in table 2:

TABLE 2

| Composition | Pearl rating |
|---|---|
| 4 | Excellent |
| 5 | Excellent |
| 6 | Excellent |
| 7 | Excellent |
| 8 | Excellent |

Example 2

Further compositions were prepared according to the method described below having the ingredients detailed in table 3. Composition 9 is of the invention. Composition 10 is comparative.

TABLE 3

| | | Composition | |
|---|---|---|---|
| | Component (wt % active) | 9 | 10 (comparative) |
| A | D.I Water | 46.11 | 46.11 |
| A | Sodium Benzoate | 0.5 | 0.5 |
| A | EDDS | 0.19 | 0.19 |
| A | CAPB | 7.2 | 7.2 |
| B | 50% Citric Acid | 0.15 | 0.15 |
| C | SLMI | 6.7 | |
| C | SCI | | 6.7 |
| D | EGDS | 24.0 | 24.0 |
| E | D.I Water | 15.0 | 15.0 |

SCI is was provided as a solid ingredient comprising 85% active Sodium Cocoyl Isethionate.

The remaining ingredients are as described in example 1.

Method

1. Component "A" ingredients were mixed until a clear and homogeneous composition was obtained. The deionized water component of ingredients A includes the water that forms part of the ingredient added as solutions and additional water added separately.
2. The pH of the system was adjusted to 4.8-5.2 with citric acid solution and then heated with mixing to 45-50° C.
3. Component "C" ingredients were added and heating was continued to 70-80° C. with rapid but smooth mechanical mixing.
4. Component "C" ingredients were added with rapid but smooth mechanical agitation. Heating was continued to 85° C. with rapid but smooth agitation. The temperature was maintained for 20+ minutes and then the heat source was removed. Cooling was carried out with rapid but smooth agitation until the system reaches a temperature of 45-50° C. (system starts to settle into a lotion/paste).
5. With rapid but smooth agitation, 20-25° C. water was slowly blended in and cooling continued to 25° C. with rapid but smooth agitation.

The compositions obtained had the properties listed in table 4.

TABLE 4

| | Composition 9 | Composition 10 |
|---|---|---|
| Appearance @ 25° C. | Thin, White Liquid/Lotion | Thick, gooey paste |
| Brookfield Viscosity @ 25° C.: | | |
| No 5 Sp. @ 2.5 RPM | 4100 cps | 120600 cps |
| No 5 Sp. @ 5 RPM | 3040 cps | 69800 cps |

Composition 9 rapidly dispersed and provided a composition having an excellent pearl quality and composition 10 was very slow to disperse.

Unlike composition 10, composition 9 is readily pourable meaning that it is easier to handle and has an improved environmental profile since heating is not required to manipulate the composition.

What is claimed is:

1. A pearlizing concentrate composition consisting of:
(a) at least 10 wt % of a glycol ester of a fatty acid;
(b) from 0.1 wt % to 18 wt % of at least one acyl alkyl isethionate surfactant of formula (I):

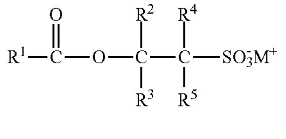
(I)

wherein $R^1$ represents an optionally substituted $C_4$-$C_{36}$ hydrocarbyl group;
each of $R^2$, $R^3$, $R^4$ and $R^5$ independently represents hydrogen or a $C_1$-$C_4$ alkyl group and wherein at least one of $R^2$, $R^3$, $R^4$ and $R^5$ is not hydrogen; and $M^+$ represents a cation;
(c) from 0.1 wt % to 30 wt % of at least one zwitterionic or amphoteric surfactant selected from the group consisting of: betaines, alkyl betaines, alkylamidopropyl betaines, cocamidopropyl betaine, alkylamidopropyl hydroxy sultaines, alkylamphoacetates, alkylamphodiacetates, alkyl propionates, alkylamphodipropionates, alkylamphopropionates, alkyliminodipropionates and alkyliminodiacetates; and
(d) optionally one or more further components selected from the group consisting of chelating agents, preservatives, pH modifiers, hydrotropes, and solvents;
wherein the concentrate composition has a viscosity of from 1000 to 50000 cPs.

2. The concentrate composition of claim 1 wherein component (a) comprises a monoester of stearic acid and/or a diester of stearic acid.

3. The concentrate composition of claim 1 which comprises from 10 to 35 wt % component (a).

4. The concentrate composition of claim 1 wherein component (b) comprises an acyl alkyl isethionate surfactant of formula (I) selected from the group consisting of sodium lauroyl methyl isethionate, sodium cocoyl methyl isethionate and sodium oleoyl methyl isethionate.

5. The concentrate composition of claim 1 which comprises from 0.5 to 15 wt % component (b).

6. The concentrate composition of claim 4 which comprises from 0.5 to 15 wt % component (b).

7. The concentrate composition of claim 1 wherein component (c) comprises at least one zwitterionic or amphoteric surfactant selected from the group consisting of cocoamidopropyl betaine and cocoamidopropylhydroxy sultaine.

8. The concentrate composition of claim 1 which comprises from 0.5 to 25 wt % component (c).

9. A method of preparing a concentrate composition, the method comprising the steps of:
(i) admixing components consisting of:
(a) at least 10 wt % of a glycol ester of a fatty acid;
(b) from 0.1 wt % to 18 wt % of at least one acyl alkyl isethionate surfactant of claim 1; and
(c) from 0.1 wt % to 30 wt % of at least one zwitterionic or amphoteric surfactant selected from the group consisting of: betaines, alkyl betaines, alkylamidopropyl betaines, cocamidopropyl betaine, alkylamidopropyl hydroxy sultaines, alkylamphoacetates, alkylamphodiacetates, alkyl propionates, alkylamphodipropionates, alkylamphopropionates, alkyliminodipropionates and alkyliminodiacetates; and
(d) optionally one or more further components selected from the group consisting of chelating agents, preservatives, pH modifiers, hydrotropes, and solvents;
(ii) heating the mixture obtained in step (i) to a temperature of at least 60° C.; and slowly cooling the composition;
wherein said concentrate composition has a viscosity of from 1000 to 50000 cPs.

10. The method of claim 9 wherein water is added in step (i) to provide an aqueous composition.

11. The method of claim 9 wherein the mixture is heated in step (ii) to a temperature of at least 75° C.

12. The method of claim 9 wherein the composition is agitated as it is cooled during step (iii) by the application of shear forces.

13. A method of providing a pearlescent finish to a formulation, the method comprising admixing into the formulation a pearlizing composition comprising the concentrate composition of claim 1.

14. The method of claim 13 which is carried out at a temperature of less than 30° C.

15. A method of preparing a pearlescent formulation, the method comprising:
(x) preparing a formulation which is not pearlescent; and
(y) adding the concentrate composition of claim 1 to the formulation which is not pearlescent prepared in step (x).

16. The concentrate composition of claim 1 which consists of:
(a) from 10 wt % to 40 wt % of a glycol ester of a fatty acid and one or more glycols selected from the group consisting of ethylene glycol, propylene glycol and butylene glycol;
(b) from 0.5 wt % to 15 wt % of at least one acyl alkyl isethionate surfactant of formula (I):

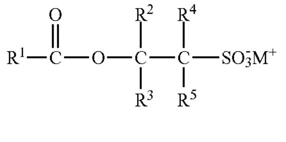
(I)

wherein $R^1$ is the residue of a fatty acid, and wherein one of the groups $R^2$, $R^3$, $R^4$ and $R^5$ represents a $C_1$-$C_4$ alkyl group and the remaining groups are hydrogen;

(c) from 0.1 wt % to 30 wt % of at least one zwitterionic or amphoteric surfactant selected from the group consisting of: betaines, alkyl betaines, alkylamidopropyl betaines, cocamidopropyl betaine, alkylamidopropyl hydroxy sultaines, alkylamphoacetates, alkylamphodiacetates, alkyl propionates, alkylamphodipropionates, alkylamphopropionates, alkyliminodipropionates and alkyliminodiacetate; and (d) optionally one or more further components selected from the group consisting of chelating agents, preservatives, pH modifiers, hydrotropes, and solvents;

wherein the concentrate composition has a viscosity of from 1000 to 50000 cPs.

* * * * *